United States Patent
Beghini et al.

(10) Patent No.: US 7,480,575 B2
(45) Date of Patent: Jan. 20, 2009

(54) METHOD FOR DETECTING MECHANICAL FEATURES OF A MATERIAL AND APPARATUS THAT CARRIES OUT THIS METHOD

(75) Inventors: Marco Beghini, Pisa (IT); Leonardo Bertini, Pisa (IT); Virgilio Fontanari, Cognola (IT)

(73) Assignee: S.M. Scienzia Machinale S.R.L., Navaochio (IT)

( * ) Notice: Subject to any disclaimer, the term of this patent is extended or adjusted under 35 U.S.C. 154(b) by 207 days.

(21) Appl. No.: 11/597,752

(22) PCT Filed: Aug. 1, 2005

(86) PCT No.: PCT/IB2005/002275

§ 371 (c)(1), (2), (4) Date: Jan. 4, 2007

(87) PCT Pub. No.: WO2006/013450

PCT Pub. Date: Feb. 9, 2006

(65) Prior Publication Data

US 2008/0033665 A1    Feb. 7, 2008

(30) Foreign Application Priority Data

Jul. 30, 2004  (IT)  ............................. TO2004A0535

(51) Int. Cl.
   *G01L 1/00* (2006.01)
(52) U.S. Cl. ....................................................... 702/42
(58) Field of Classification Search .................... 702/42
   See application file for complete search history.

(56) References Cited

U.S. PATENT DOCUMENTS

2005/0170274 A1*  8/2005  Matsumura et al. ......... 430/126
2007/0205001 A1*  9/2007  Shuster et al. .............. 166/380

* cited by examiner

Primary Examiner—Tung S Lau
Assistant Examiner—Aditya S Bhat
(74) Attorney, Agent, or Firm—Dennison, Schultz & MacDonald (57) ABSTRACT

A method for detecting mechanical features of a material, in particular a metal material, provides a preliminary step where a database is created containing a finite number of reference curves (P,h) (52). Such curves are obtained using a finite elements analysis and reproduce the trend of the applied force (P) responsive to the penetration depth (h) during an indentation test. The reference curves (P,h) are obtained for a determined number of different materials having a known elastic modulus E, and values of yield stress ($\sigma_{sn}$) and strain-hardening coefficient (n) comprised within determined ranges. The tested sample is then arranged at an indenter, for example a ball indenter (52), for being subject to an indentation test. This is started to cause a graduated penetration of the indenter in the material subject to analysis (53). During the indentation test the penetration depth (h) responsive to the penetration force (P) are measured, and a succession of measured couples (P,h) (54) is then recorded. Such couples of determined values (P,h) are then computed (55), in order to extrapolate from the database at least one reference curve (P,h), for example by a least squares method (56).

16 Claims, 5 Drawing Sheets

METHOD FOR DETECTING MECHANICAL FEATURES OF A MATERIAL AND APPARATUS THAT CARRIES OUT THIS METHOD

This application is a filing under 35 USC 371 of PCT/IB2005/002275, filed Aug. 1, 2005.

FIELD OF THE INVENTION

The present invention relates to an apparatus for detecting mechanical features of a material, in particular a metal material.

DESCRIPTION OF THE PRIOR ART

As well known, for detecting mechanical features of a metal material, hardness tests exist that are executed on samples by an element having high hardness (indenter) that is pushed, with a controlled contact force P, against a surface of the sample for causing a permanent deformation on it.

Hardness, in any case, is not considered sufficient to define the material, since it represents essentially a technological feature. Indeed, for describing satisfactorily the mechanical features of a metal material, the following parameters are used: yield stress $\sigma_{sn}$, strain-hardening coefficient n and elastic modulus E (Young's modulus). In fact, a strain-stress curve $\sigma$-$\epsilon$ that describes graphically the features of a metal material is fully definable on the basis of such parameters, for example according to the known Hollomon equation:

$$\sigma = \begin{cases} E \cdot \varepsilon & \varepsilon \leq \dfrac{\sigma_{sn}}{E} \\ \sigma_{sn}^{(1-n)} \cdot E^n \cdot \varepsilon^n & \varepsilon > \dfrac{\sigma_{sn}}{E} \end{cases}$$

In addition to the elastic modulus, which is a known starting parameter for a material or in any case a parameter obtainable with non-destructive tests, the other two parameters, i.e. the yield stress $\sigma_{sn}$ and the strain-hardening coefficient n, are obtained from the so called tensile test. This test, as well known, is a destructive test and is not appropriate for determining the features of a material of which a suitable sample for the tensile test is not available, for example a weld bead.

Furthermore, the tensile test is effected by means of complex and expensive apparatus requiring a manual procedure both for preparing the sample and for the execution of a test. In particular, the tensile test is not suitable for an automatic determination procedure of the features of a material.

SUMMARY OF THE INVENTION

It is therefore a feature of the invention to provide a method for determining mechanical features of a material, such as the yield stress csn and the strain-hardening coefficient n, in particular, of a metal material, which is capable of working in a completely automatic way and without the need of a destructive test on the material.

It is another feature of the invention to provide such a method that allows to obtain the yield stress and the strain-hardening coefficient of a material with a quick, easy and cheap measure.

It is a further feature of the invention to provide such a method for executing tests on samples whose mechanical characteristics are variable locally, such as the welded surfaces where a traditional tensile test would be impossible.

It is another feature of the invention to provide an apparatus that carries out the aforementioned method and presents the same advantages.

These and other features are accomplished with one exemplary method for detecting mechanical features of a material, in particular a metal material, comprising the following steps:

prearranging an indenter suitable for penetrating in a sample of a material to analyse for a measurable depth (h) with a measurable force (P);

creating a database comprising a finite number of reference curves (P,h) reproducing the trend of the applied force (P) responsive to the penetration depth (h), said database being built starting from values of yield stress ($\sigma_{sn}$) and strain-hardening coefficient (n) for a determined number of materials for which said values are known;

carrying out an indentation test on the sample to analyse by said indenter through detecting and recording values of force (P) and depth (h) at a plurality of successive instants during the penetration of said instrument in the sample, obtaining a succession of couples of determined values (P,h) for each measuring step;

analysing the succession of couples of determined values (P,h) and selecting from said database at least one of said reference curves (P,h);

displaying the values of the parameters of interest, in particular, strain-hardening coefficient (n) and yield stress ($\sigma_{sn}$), corresponding to said or each reference curve (P,h).

In particular, the execution of a test is stopped at a maximum value of penetration $hs_{MAX}$, modifiable at setup, for starting a step of analysing the obtained data.

The yield stress $\sigma_{sn}$ and the strain-hardening coefficient n can be computed to obtain a strain-stress curve ($\sigma$-$\epsilon$) for the examined sample.

In particular, the analysis of the succession of couples of determined values (P,h) provides at least one of the following steps:

defining a starting bidimensional search domain $\Omega$ having a first dimension defined by the yield stress $\sigma_{sn}$ and a second dimension defined by the strain-hardening coefficient n;

dividing an actual bidimensional domain $\Omega$ into a plurality of portions by a matrix structure having K, L axes intersecting the first and the second dimension for increasing values of the yield stress $\sigma_{sn}$ and of the strain-hardening coefficient n, the intersection between an axis K and an axis L identifying a point of intersection J defined by a couple of coordinates $\sigma_{sn\text{-}J}$ and $n_J$;

computing a curve $Pt_J = ft(E, \sigma_{sn\text{-}J}, n_J, h)$ for each point J of said matrix;

comparing each curve $Pt_J = ft(E, \sigma_{sn\text{-}J}, n_J, h)$ calculated on said matrix with the curve fs detected experimentally;

selection of a curve that is nearest to that detected experimentally.

The starting domain extends, in particular, up to a maximum value of the yield stress $\sigma_{sn\text{-}MAX}$ and up to a maximum value of the strain-hardening coefficient $n_{MAX}$.

Preferably, the curve $Pt = ft(E, \sigma_{sn}, n, h)$ is calculated according to the equation:

$$Pt(E, \sigma_{sn}, n, h) = E \cdot D^2 \sum_{k=1}^{4} A_k \cdot \left(\frac{h}{D}\right)^{\frac{k}{2}}$$

wherein $\sigma_{sn}$ is the actual yield stress;

E represents the elastic modulus associated to the tested material;

$A_k$ is a function of the strain-hardening coefficient n and of the yield stress $\sigma_{sn}$;

D is the diameter of the indenter 15;

h is a variable that represents the penetration; and

Pt is a variable that represents the force of contact.

Preferably, the strain-stress curve σ-ε is determined using the Hollomon equation:

$$\sigma = \begin{cases} E \cdot \varepsilon & \varepsilon \leq \dfrac{\sigma_{sn}}{E} \\ \sigma_{sn}^{(1-n)} \cdot E^n \cdot \varepsilon^n & \varepsilon > \dfrac{\sigma_{sn}}{E} \end{cases}$$

where $\sigma_{sn}$ represents the measured yield stress (260);

n is the strain-hardening coefficient (260); and

E is the elastic modulus.

Advantageously, the selection of the succession of couples of determined values (P,h) with subsequent extraction from the database of at least one reference curve (P,h) is started by the introduction of a reference parameter for the sample, in particular of the elastic modulus, and in order to identify the class of the metal material narrowing the field of the analysis.

The step of selection can be advantageously executed by the least squares method.

In particular, the selection of a curve (P,h) can provide an interpolation of the values of the parameters corresponding to two reference curves (P,h), unless a reference curve (P,h) exists capable of approximating the succession of the determined couples (P,h) with sufficient precision.

Preferably, the creation of the database of reference curves (P,h) is effected by a finite elements analysis capable of simulating with high precision the behaviour of a determined number of materials. This way, it is possible to obtain a high number of theoretical reference curves (P,h), capable of providing the necessary data concerning the mechanical features of the material without testing them and then with high savings versus costs and time.

According to another aspect of the invention, an apparatus for detecting mechanical features of a material, in particular a metal material, provides:

an indenter operated by motor means movable towards a sample to test;

means for measuring the contact force P applied by the indenter to the sample and the penetration h of the indenter in the deformed sample with respect to a reference system, computer control means comprising:

acquisition means suitable for measuring at successive instants ($t_1, t_2, t_3, \ldots t_i, \ldots t_N$) the actual values of the contact force P and of the penetration h, generating couples of data ($Ps_1,hs_1$), ($Ps_2,hs_2$), ($Ps_3,hs_3$), ... ($Ps_1, hs_1$) ... ($Ps_N,hs_N$) that define together a curve fs detected experimentally Ps=fs(hs) of the contact force P versus the penetration h;

correlation means suitable for executing a searching and comparing step for selecting, among a plurality M of determined theoretical curves $Pt_1=ft_1(h), Pt_2=ft_2(h), \ldots Pt_j=ft_j(h), \ldots Pt_M=ft_M(h)$, one curve that better approximates the experimentally measured values, said correlation means (140) being suitable for giving as output the yield stress $\sigma_{sn}$ and the strain-hardening coefficient n associated to the selected curve thus obtaining the yield stress $\sigma_{sn}$ and the strain-hardening coefficient n of the material of the tested sample.

Preferably, the indenter used is a ball indenter.

In this way an advantage is achieved with respect to the known systems, since the yield stress $\sigma_{sn}$ and the strain-hardening coefficient n are obtained from a particular hardness test that is an easy, cheap, non-destructive test and uses a low complexity apparatus.

BRIEF DESCRIPTION OF THE DRAWINGS

The invention will now shown with the following description of an exemplary embodiment thereof, exemplifying but not limitative, with reference to the attached drawings wherein.

DESCRIPTION OF THE PREFERRED EMBODIMENTS

Figure 1:
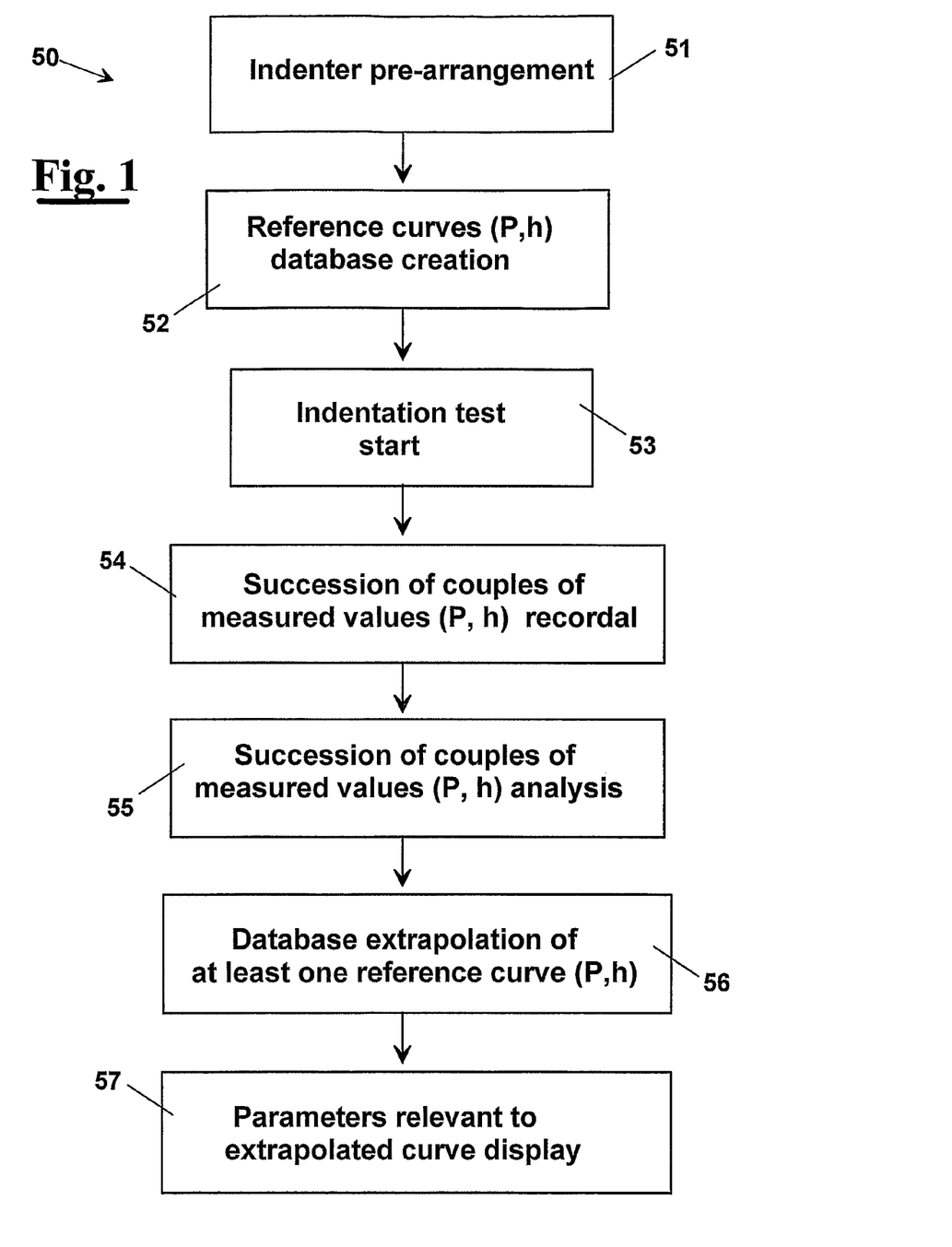
FIG. 1 shows diagrammatically an apparatus for detecting mechanical features of a material, in particular a metal material, according to the present invention.

With reference to the block diagram 50 shown in FIG. 1, an exemplary method for detecting mechanical features of a material, in particular a metal material, according to the invention, comprises the steps described hereafter. The process for determining the mechanical features of the sample provides a preliminary step where a database is built containing a finite number of reference curves (P,h), block 52. Each of such curves is obtained using a finite elements analysis, well known to a skilled person and then not described in more detail, and reproducing the trend of the applied force (P) responsive to the penetration depth (h) during an indentation test. The reference curves (P,h) are obtained for a determined number of different materials having a known E elastic modulus, and having yield stress ($\sigma_{sn}$) and strain-hardening coefficient (n) comprised within determined ranges.

The tested sample is then arranged at an indenter apparatus, for example a ball indenter, block 52, for being subject to an indentation test. The test is started causing a graduated penetration of the indenter in the tested material, block 53. During the indentation test the penetration depth (h) is determined responsive to the penetration force (P), and the succession of couples (P,h) measured is then recorded, block 54. Such couples of determined values (P,h) are then computed, block 55, in order to extrapolate from the database at least one reference curve (P,h), for example a least squares method, block 56. Once a most relevant reference curve for the determined succession of couples (P,h) has been retrieved, the corresponding values of the parameters of interest are displayed, block 57.

If there are two curves that approximate the trend of the force P responsive to the depth h for the tested sample, the values of the parameters of interest are determined by an interpolation of the corresponding values of the two reference curves. This remarkably reduces the errors giving high precision results.

Figure 2:
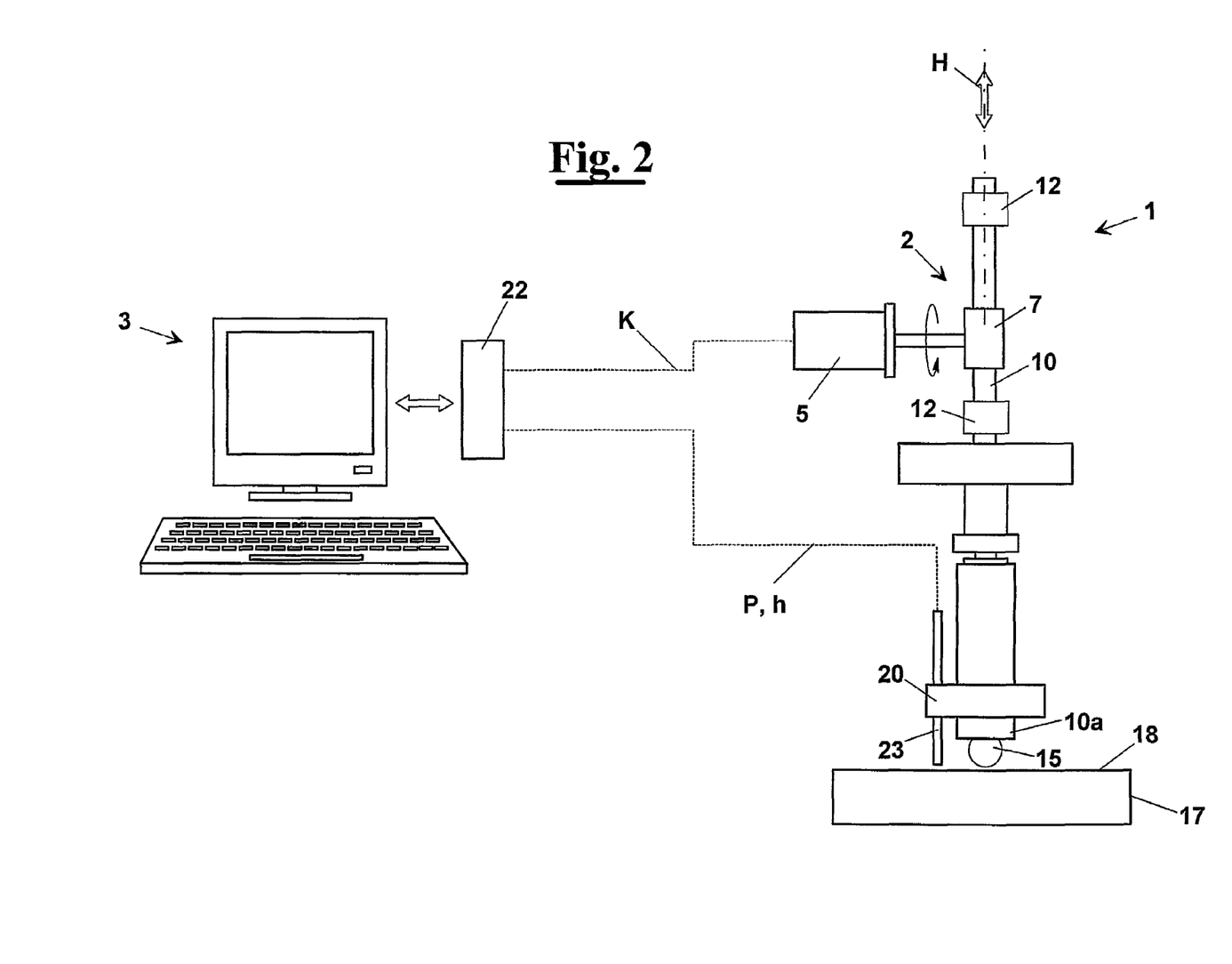
FIGS. 2 and 3 show measuring operations executed by the apparatus of FIG. 1.

With reference to FIG. 2, an apparatus 1 is shown capable of carrying out the steps of the method above described. The apparatus 1 comprises essentially a measuring device 2 controlled by a computer 3. The measuring device 2 provides a controlled actuator 5 (for example a step motor or a position controlled gear motor) that, through a transmission 7 (for example a transmission of the pinion gear-rack or nut-screw type) that changes the speed of the controlled actuator 5 in a linear reversible movement, moves a slider 10 along a vertical direction H. The slider 10 is supported by a guide 12 held by a support structure (not shown) and causes a free end 10a thereof to move along with a ball indenter 15 made of ceramic material with high elastic modulus, for example tungsten carbide. The ball indenter 15 is suitable for being pushed against a sample 17 to test. More in detail, the ball indenter 15 penetrates into a plane surface 18 of the sample 17 that is substantially orthogonal to the direction H.

The indenter 15 is firstly approached, then put into contact and then caused to penetrate the sample 17 with a controlled speed that is extremely low (a few mm/minute). Ball indenter 15 is coupled to a load cell 20 (of known type) which outputs an electric signal Ps responsive to the contact force applied by indenter 15 to sample 17. Load cell 20 preferably has a resolution of at least 0.1 Newton. The electric signal Ps is sent to an interface device 22 and in turn to computer 3.

The measuring apparatus 1 is, furthermore, provided with a position measuring device 23 of optical type that detects a penetration value h. This penetration h is responsive to how much the indenter 15 has sunk into the sample 17 with respect to a reference system (for example the starting surface 18). This penetration h can be preferably expressed by a maximum value of penetration detected with respect to the reference. The penetration steps are carried out with high precision, preferably with a resolution of at least $10^{-3}$ mm. The penetration signal as determined hs is sent to interface device 22 and in turn to computer 3. Interface device 22 furthermore, guides drive signals K from computer 3 to controlled actuator 5.

Owing to the contact between indenter 15 and sample 17, the data acquisition and control program stores at predetermined instants the contact force Ps and the penetration $h_s$ as measured.

Figure 3:
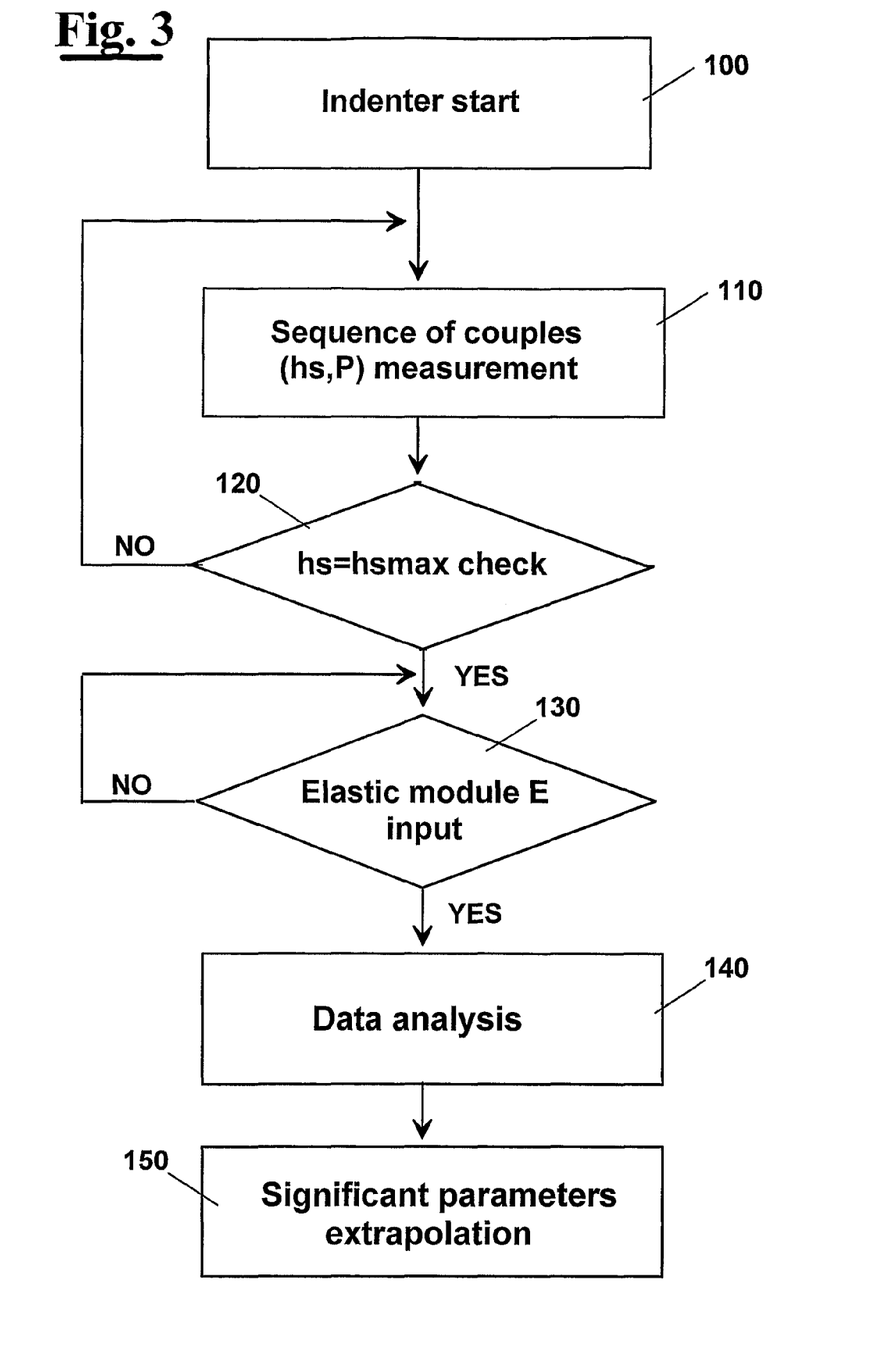

In FIG. 3 the procedure of acquisition and control is diagrammatically shown executed according to the method provided by the present invention. The indentation test begins with starting the controlled movement of the indenter towards the sample, block 100. From this instant the values of the contact force P and of the penetration h to it associated are measured, block 110. This step is carried out up to a maximum value of penetration $hs_{MAX}$, which can be changed at setup, and then, block 120, the operations of data acquisition are stopped for starting the operations of controlling the obtained data. This way, at the output of block 120, n couples of data are available measured at consecutive instants $t_1, t_2, t_3, \ldots t_i, \ldots t_N$, i.e. $(Ps_1, hs_1), (Ps_2, hs_2), (Ps_3, hs_3)- \ldots (Ps_i, hs_i) \ldots (Ps_N, hs_N)$, that define together a curve fs detected experimentally: Ps=fs(hs). This curve concerns contact force P versus penetration h as above described. Block 130 is a standby step where the indication of the class of the tested material versus elastic modulus E is awaited. In particular, as known, different classes exist, among which: light alloys, copper alloys, iron alloys and/or other material, even non metallic material, whose curve σ-ϵ can be defined with a three parameters expression that comprise elastic modulus, yield stress and strain-hardening coefficient (as for example, but not exclusively, the Hollomon equation).

The introduction of the class of material allows to execute, in a completely automatic way, a searching and comparing step (matching or likelihood or neighbouring comparison), block 140, in order to extrapolate among a plurality M of theoretical curves, a curve capable of best approximating the experimental curve Ps=fs(hs) described by the couples $(Ps_i, hs_i)$, block 150. At the end of this step, values are identified of the yield stress $\sigma_{sn}$ and the strain-hardening coefficient n associated to the selected curve. Such values are then given to the material of the tested sample.

By the yield stress $\sigma_{sn}$ and the strain-hardening coefficient n provided as output the strain-stress curve σ-ϵ is calculated and shown on the computer 3.

Figure 4:
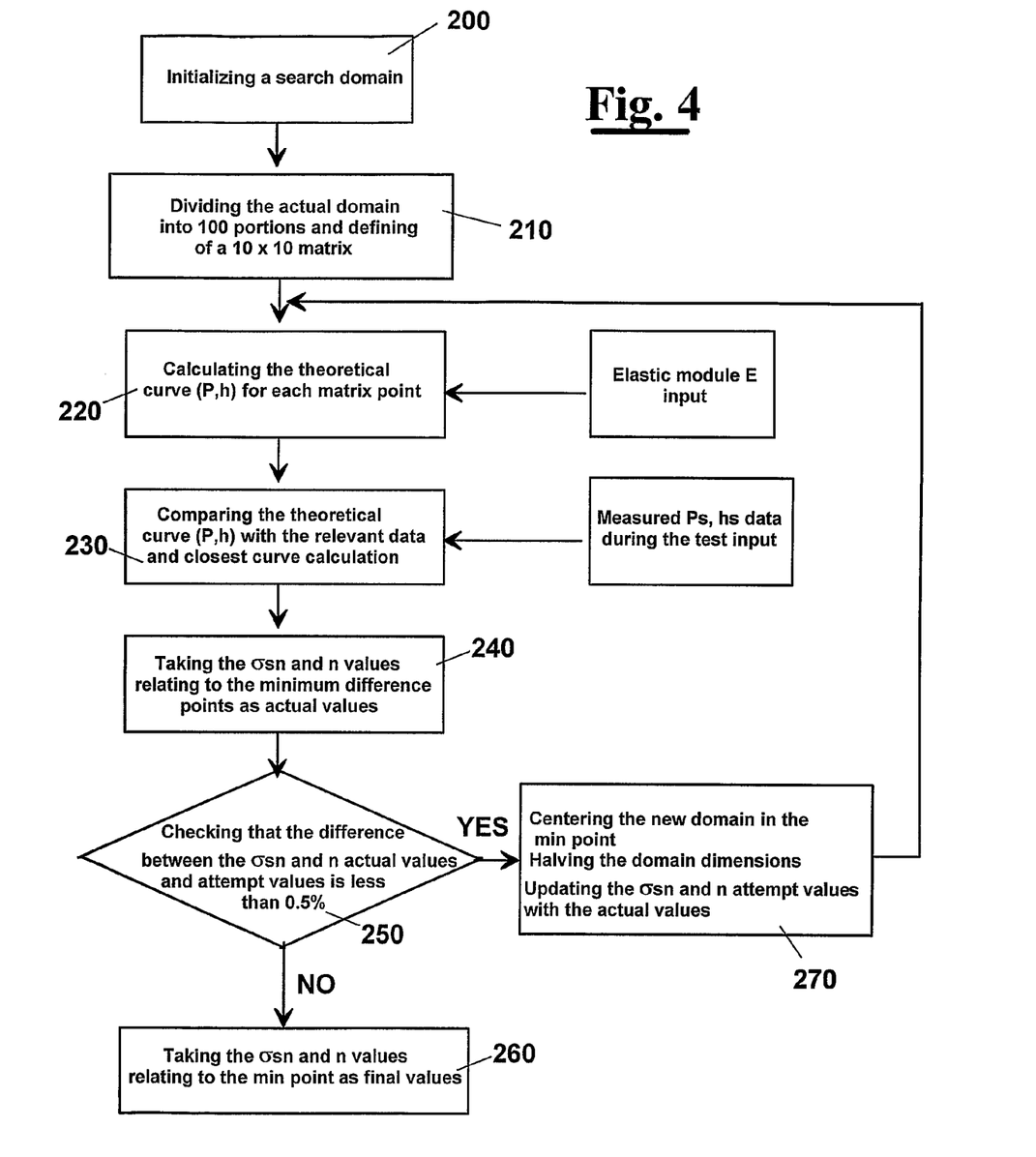
FIG. 4 shows a step executed by the apparatus of FIG. 1.
Figure 5:
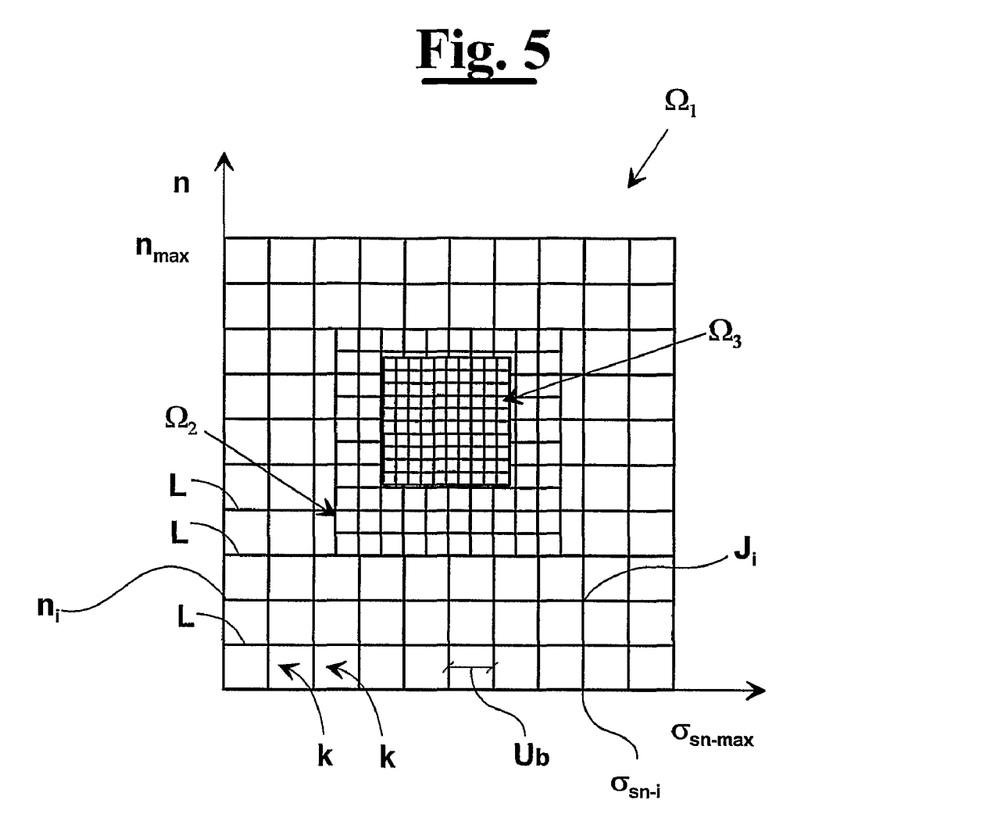

With reference to FIG. 4, the steps are shown with more detail of controlling the data by block 140. Such operations provide the generation of a bidimensional search domain Ω, block 200, having as dimensions the yield stress $\sigma_{sn}$ and the strain-hardening coefficient n (FIG. 5). The domain extends up to a maximum value of yield stress $\sigma_{sn-MAX}$ and to a maximum value of strain-hardening coefficient $n_{MAX}$. This bidimensional search domain can be shown in a Cartesian plane with a rectangle having as abscissa the yield stress $\sigma_{sn}$ and as ordinate the strain-hardening coefficient n. An actual bidimensional domain Ω is divided into a plurality of portions, for example a hundred, by a rectangular matrix having K, L axes crossing the axis of the abscissas and of the ordinate for increasing values of the yield stress $\sigma_{sn}$ and of the strain-hardening coefficient n, block 210. Such values are increasing for multiple integers of a unit base Ub of fixed value. The matrix thus formed has square (or generically rectangular) framework. The intersections between an axis K and an axis L defines a point J having a couple of coordinates $\sigma_{sn-J}$ and $n_J$.

By a continuous equation a curve $Pt_J=f_t(E, \sigma_{sn-J}, n_J, h)$ is calculated for each point J of the matrix. This is made according to the values $\sigma_{sn-J}$ and $n_J$ that define the point of intersection J and to the elastic modulus E associated to the chosen class of material, block 220.

Preferably, but not exclusively, the following equation is used:

$$Pt(E, \sigma_{sn}, n, h) = ft(E, \sigma_{sn}, n, h) = E \cdot D^2 \sum_{k=1}^{4} A_k \cdot \left(\frac{h}{D}\right)^{\frac{k}{2}}$$

where $\sigma_{sn}$ is the actual yield stress;

E represents the elastic modulus associated to the class of material selected by the user;

$A_k$ is a variable function of the actual strain-hardening coefficient n and of the yield stress $\sigma_{sn}$; such $A_k$ functions are recorded in a data-base that is resident in the control software.

D is the diameter of the indenter 15;

h is a variable that represents the theoretical penetration; and

Pt is a variable that represents the contact force (theoretical).

Then a comparison is made of each curve $Pt_J=ft(E, \sigma_{sn-J}, n_J, h)$ calculated on the matrix with the curve $f_s$ detected experimentally: Ps=fs(hs), eventually selecting the curve that is closest to that detected experimentally, block 230.

Preferably as index of error is used the following (non negative) equation:

$$diff(\sigma_{sn-J}, n_J) = \sum_{i=1}^{n} [Ps_i - Pt_J(E, \sigma_{sn-J}, n_J, hs_i)]^2$$

where $Ps_i$ is the force of the $i^{th}$ experimentally determined point;

$hs_i$ represents the penetration of the $i^{th}$ experimentally determined point;

Pt represents the force of the $i^{th}$ measured point as can be deducted from the model calculated at point J of the matrix; and E is the elastic modulus, thus determining a point $J_{MIN}$ of the matrix to which the nearest curve to that measured is associated (least squares method).

The coordinates $\sigma_{sn\text{-}JMIN}$ and $n_{JMIN}$ belonging to the selected curve and defining the point $J_{MIN}$ are taken as actual values, block 240. Then a verification is carried out for checking whether the approximation fulfils determined conditions. In case of positive verification, block 260, the actual values of the coordinates $\sigma_{sn\text{-}JMIN}$ and $n_{JMIN}$ are taken as final. For example, a control can be carried out on the number of iterations and/or a comparison can be executed among the actual values $\sigma_{sn\text{-}corr}$ and the previous values, i.e. calculated in the previous iteration $\sigma_{sn\text{-}prec}$, for calculating a relative difference:

$$|\sigma_{sn\text{-}corr} - \sigma_{sn\text{-}prec}|/\sigma_{sn\text{-}corr}$$

that is compared with a threshold value for defining the output of block 250. Similar operations can be done on the strain-hardening coefficient n.

In case of negative verification, block 270, a domain is defined having centre in the actual coordinates $\sigma_{sn\text{-}MIN}$ and $n_{JMIN}$ and having size half than the previously used domain. Also unit base that is used for dividing the domain is halved. From the block 270 the flow returns back to block 220 for repeating the iteration of the previously shown operations.

The representation of the final strain-stress curve σ-ε is obtained using the Hollomon equation (or other equivalent equation with the three parameters):

$$\sigma = \begin{cases} E \cdot \varepsilon & \varepsilon \leq \dfrac{\sigma_{sn\text{-}JMIN}}{E} \\ \sigma_{sn\text{-}JMIN}^{(1-n_{JMIN})} \cdot E^{n_{JMIN}} \cdot \varepsilon^{n_{JMIN}} & \varepsilon > \dfrac{\sigma_{sn\text{-}JMIN}}{E} \end{cases}$$

where $\sigma_{sn\text{-}JMIN}$ represents the yield stress defined at the output of block 260;

$n_{JMIN}$ is the strain-hardening coefficient defined at the output of block 260; and E is the elastic modulus.

The advantages achieved by the apparatus and by the method according to the present invention are many, and in particular:

the yield stress and the strain-hardening coefficient are obtained through a quick, easy and cheap measure;

the measure is easily executed also on a final product without destroying it (instead of the tensile test that is always a test of destructive type); and the apparatus can test samples where the mechanical features are variable locally (for example weld seams)—in this case a traditional tensile test would be impossible.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

The invention claimed is:

1. Method for detecting mechanical features of a material, in particular a metal material, characterised in that it comprises the following steps:

prearranging an indenter suitable for penetrating in a material to analyse for a measurable depth (h) with a measurable force (P);

creating a database comprising a finite number of reference curves (P,h) reproducing the trend of the applied force (P) responsive to the penetration depth (h), said database being built starting from values of yield stress ($\sigma_{sn}$) and strain-hardening coefficient (n) for a determined number of materials for which said values are known;

carrying out an indentation test on a sample to analyse by said indenter through detecting and recording the values of force (P) and depth (h) at a plurality of successive instants during the penetration of said instrument in the sample, obtaining a succession of couples of determined values (P,h) for each measuring step;

analysing the succession of couples of determined values (P,h) and selecting from said database of at least one of said reference curves (P,h);

displaying the values of the parameters of interest, in particular, elastic modulus (E), strain-hardening coefficient (n) and yield stress ($\sigma_{sn}$) corresponding to said or each reference curve (P,h).

2. Method, according to claim 1, wherein the execution of said test is stopped at a predetermined maximum value of penetration $hs_{max}$.

3. Method, according to claim 1, wherein a step is provided of controlling said yield stress $s_{sn}$ and strain-hardening coefficient n suitable for providing a strain-stress curve (s-e) for said examined sample.

4. Method, according to claim 3, wherein said strain-stress curve σ-e is determined using the Hollomon equation:

$$\sigma = \begin{cases} E \cdot \varepsilon & \varepsilon \leq \dfrac{\sigma_{sn}}{E} \\ \sigma_{sn}^{(1-n)} \cdot E^{n} \cdot \varepsilon^{n} & \varepsilon > \dfrac{\sigma_{sn}}{E} \end{cases}$$

where $\sigma_{sn}$ represents the measured yield stress (260)

n the strain-hardening coefficient determined (260); and

E is the elastic modulus.

5. Method, according to claim 1, wherein said step of controlling said succession of couples of determined values (P,h) provides at least one of the following steps:

defining a starting bidimensional search domain W having a first dimension defined by the yield stress $\sigma_{sn}$ and a second dimension defined by the strain-hardening coefficient n;

dividing an actual bidimensional domain W into a plurality of portions by a matrix having K, L axes intersecting the first and the second dimension for increasing values of the yield stress $\sigma_{sn}$ and of the strain-hardening coefficient n, the intersection between an axis K and an axis L identifying a point of intersection J defined by a couple of coordinates $\sigma_{sn\text{-}J}$ and $n_J$;

computing a curve $Pt_J = ft(E, \sigma_{sn\text{-}J}, n_J, h)$ for each point J of said matrix;

comparing each curve $Pt_j=ft(E,\sigma_{sn\text{-}j},n_j,h)$ calculated on said matrix with the curve fs detected experimentally;

selecting a curve nearest to that experimentally detected.

6. Method, according to claim 5, wherein said starting domain extends up to a maximum value $\sigma_{sn\text{-}MAX}$ of the yield stress and up to a maximum value $n_{MAX}$ of the strain-hardening coefficient.

7. Method, according to claim 5, wherein said curve $Pt=ft(E,\sigma_{sn},n,h)$ is calculated according to the equation:

$$Pt(E, \sigma_{sn}, n, h) = E \cdot D^2 \sum_{k=1}^{4} A_k \cdot \left(\frac{h}{D}\right)^{\frac{k}{2}}$$

where $\sigma_{sn}$ is the actual yield stress;

E represents the elastic modulus associated to the tested material;

$A_k$ is a function of the strain-hardening coefficient n and of the actual yield stress $\sigma_{sn}$;

D is the diameter of said indenter;

h is a variable that represents the penetration; and

Pt is a variable that represents the force of contact.

8. Method, according to claim 1, wherein said selection of said succession of couples of determined values (P,h) with subsequent extraction of at least one reference curve (P,h) from said database is started by the introduction of a reference parameter for said sample.

9. Method, according to claim 1, wherein said selection of said or each reference curve (P,h) from said database is effected by the least squares method.

10. Method, according to claim 1, wherein said step of displaying said parameters of interest provides an interpolation of the values of the parameters corresponding to two reference curves (P,h).

11. Method, according to claim 1, wherein said step of creating said database of reference curves (P,h) is effected by a finite elements analysis capable of simulating with high precision the behaviour of a determined number of materials, said reference curve being a theoretical reference curve.

12. Apparatus for detecting mechanical features of a material, in particular a metal material characterised in that it comprises means suitable for executing the method according to claim 1.

13. Apparatus for detecting mechanical features of a material, in particular a metal material comprising:

an indenter (15) operated by motor means (5,7) movable towards a sample (17) to test;

means for measuring (20) a contact force P applied by said indenter (15) to said sample (17) and a penetration h of said indenter in the deformed sample with respect to a reference system;

characterised in that it comprises computer control means (3) having acquisition means (110,120) suitable for measuring at successive instants (t1, t2, t3, ... ti, ... tN) the actual values of the contact force Ps and of the penetration hs thus generating couples of data $(Ps_1, hs_1)$, $(Ps_2, hs_2)$, $(Ps_3, hs_3)$ ... $(Ps_i, hs_i)$ ... $(Ps_N, hs_N)$ that define together a curve fs detected experimentally Ps=fs(hs) of the contact force P versus the penetration h;

correlation means (140) suitable for executing a searching and comparing step for selecting, among a plurality M of determined theoretical curves $Pt_1=ft(h)$, $Pt_2=ft(h)$ ... $Pt_j=ft(h)$ ... $Pt_M=ft(h)$, one curve that better approximates the experimentally measured values $Ps_i$, $hs_i$, said correlation means (140) being suitable for giving as output the yield stress $\sigma_{sn}$ and the strain-hardening coefficient n associated to the selected curve thus obtaining the yield stress $\sigma_{sn}$ and the strain-hardening coefficient n of the material of the sample (17) subject to test.

14. Apparatus according to claim 13, wherein displaying means (3) are provided suitable for representing graphically the strain-stress curve σ-e associated to the yield stress $\sigma_{sn}$, and to the strain-hardening coefficient n as determined.

15. Apparatus according to claim 13, wherein said acquisition means (110,120) are suitable for measuring the penetration hs up to reaching a maximum limit of penetration $hs_{MAX}$.

16. Apparatus according to claim 13, wherein said indenter is a ball indenter.

* * * * *